United States Patent [19]

Willer et al.

[11] Patent Number: 4,878,968

[45] Date of Patent: Nov. 7, 1989

[54] OXIDIZING SALTS OF CUBYL AMINES

[75] Inventors: Rodney L. Willer, Newark; Glen T. Cunkle, Wilmington, both of Del.; Nathan Klein, Baltimore, Md.

[73] Assignee: Morton Thiokol, Inc., Chicago, Ill.

[21] Appl. No.: 143,496

[22] Filed: Jan. 12, 1988

[51] Int. Cl.[4] .................... C06B 31/00; C07C 87/40; C07C 87/453
[52] U.S. Cl. .................... 149/45; 60/210; 60/214; 60/215; 60/217; 149/46; 149/47; 149/92; 149/119; 564/458
[58] Field of Search .................... 149/45, 46, 47, 92, 149/119; 60/210, 214, 215, 217; 564/458

[56] References Cited

U.S. PATENT DOCUMENTS

| | | | |
|---|---|---|---|
| 3,558,704 | 1/1971 | Gregory | 260/563 |
| 3,700,393 | 10/1972 | Mueller | 60/214 |
| 4,402,775 | 9/1983 | Wood | 149/49 |
| 4,604,183 | 8/1986 | Edelson et al. | 208/420 |

OTHER PUBLICATIONS

Eaton, P. E., et al., Jacs. vol. 109, pp. 1268–1269 (1987).
Politzer, P., et al., Jacs, vol. 107, pp. 121–124 (1985).
Davidson, R. B., et al., Jacs, vol. 100, No. 7, pp. 2017–2021 (1978).
Edward, J. T., et al., Jacs, vol. 98, No. 11, pp. 3075–3085 (1976).
Eaton, Philip E., et al., "Synthesis of 1,4-Dinitrocubane," J. Org. Chem., 1984, vol. 49, pp. 185–186.
Eaton, Philip E., et al., "The Cubane System," J. Am. Chem. Soc., Mar. 5, 1964, vol. 86, pp. 962–964.

*Primary Examiner*—Teddy S. Gron
*Attorney, Agent, or Firm*—George Wheeler; Gerald K. White

[57] ABSTRACT

A compound having the following formula:

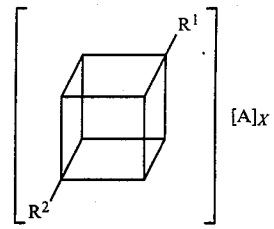

wherein $R^1$ is $-N^+H_3$ as found in claim 1 and $R^2$ is either the same as $F^1$ or hydrogen. "A" is an oxidizing anion, and X is selected to provide a neutral charge balance for the compound. A method of making a compound of the indicated structure from a compound of similar structure by an anion exchange process is also disclosed. Finally, propellant formulations incorporating the novel compounds of the present invention as fuels and oxidizers are disclosed.

8 Claims, No Drawings

OXIDIZING SALTS OF CUBYL AMINES

GOVERNMENT RIGHTS

The United States government has rights in this invention pursuant to Contract No. N00014-87-C-0068, awarded by the Office of Naval Research.

TECHNICAL FIELD

The present invention relates to propellants, particularly liquid monopropellants, and most particularly liquid gun monopropellants. The invention also relates to novel compounds having a cubane nucleus.

BACKGROUND ART

Liquid gun propellants and rocket propellants based on concentrated water solutions of hydroxylammonium nitrate (HAN) as the oxidizer and another solid or fluid material as the fuel are known. For example, U.S. Pat. No. 4,402,775, issued to Wood on Sept. 6, 1983, column 1, teaches a liquid gun bipropellant comprising HAN and a hydrocarbon fuel, mixed in the gun. Wood states that this composition requires more than 10 parts of HAN for each part of fuel. Triethanolammonium nitrate fuels for aqueous solution HAN-based monopropellants are also known. It would be useful to provide a more energetic fuel with a higher impetus and burn rate than these propellants have.

Cubane is a coined name for pentacyclo[4.2.0.0$^{2,5}$.0$^{3,8}$.0$^{4,7}$]octane. In the 1,4 orientation of substituents of cubane, the two substituents are attached to diametrically opposed corners of the cubic nucleus. All disubstituted cubanes referred to herein are 1,4-cubanes.

Various salts and compounds of cubane are known. Eaton, et al., "Synthesis of 1,4-dinitrocubane", *Journal of Organic Chemistry*, Vol. 49, No. 1, pages 185–186 (1984), and U.S. Pat. No. 3,558,704, issued to Gregory on Jan. 26, 1971, discloses the following compounds:
1,4-dinitrocubane (CAS Registry No. 87830-30-6); nitroperchlorohomocubane;
cubane-1,4-dicarboxylic acid (CAS Registry No. 32846-66-5);
1,4-diaminocubane (CAS Registry No. 87830-29-3);
1,4-bis[(tertiarybutoxycarbonyl)amino]cubane (CAS Registry No. 87830-27-1);
1,4-diaminocubane dihydrochloride (CAS Registry No. 87830-28-2);
4-methylcubane-1-amine;
4-methylcubane-1-methylamine The first paragraph of the cited Eaton article suggests that 1,4-dinitrocubane is contemplated to have good thermal stability and high density, and to be an "energetic" compound, but the article does not show the energetics of that compound or other properties relevant to its use in a propellant. On page 186, column 2, the Eaton reference contains a synthesis of 1,4-diaminocubane dihydrochloride from 1,4-bis[tertiarybutoxycarbonyl)amino]cubane, and the synthesis of the latter compound from cubane-1,4-dicarboxylic acid. The reference indicates that cubane-1,4-dicarboxylic acid is available in substantial quantities from the University of Chicago, and cites Eaton et al., *Journal of the American Chemical Society*, Vol. 86, page 962 (1964) for a synthesis of cubane-1,4-dicarboxylic acid. Cubane 1,4-dicarboxylic acid is commercially available in the form of the dimethyl ester, from Enichem Sintesi SpA., Milan, Italy.

None of the synthetic methods in the prior art known to the present inventors involve the use of anionic exchange resins, and no utility is disclosed for any of the compounds listed above, excepting the nontoxic acid addition salts of 4-methylcubane-1-amine and 4-methylcubane-1-methylamine, which are disclosed to be antiviral agents in animals.

SUMMARY OF THE INVENTION

A first aspect of the invention is a compound having the following formula:

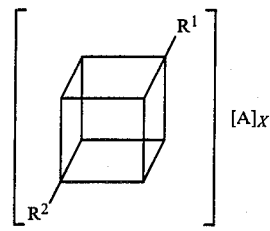

wherein R$^1$ is:

$$-N^+H_3$$

and R$^2$ is selected from R$^1$ and hydrogen. "A" is an oxidizing anion, and X is an integer providing a charge balanced composition. X is 2 divided by the valence of A if R$^1$ and R$^2$ are each the moiety identified above, and X is 1 divided by the valence of A if R$^2$ is hydrogen. Specific compounds having this generic structure are also individually claimed.

A second aspect of the invention is a method of making a compound having the receding formula, in which A is a selected oxidizing anion, from a reactant having the same formula, except that A in the reactant is not the selected oxidizing anion. (The anion of the reactant is sometimes called the "reactant anion" herein.) Such reactants are known per se, although no utility has previously been described for them. This method includes the steps of charging a basic anionic exchange resin with an oxidizing anion and contacting the charged anionic exchange resin with the previously described reactant, thereby exchanging the anion on the resin with the anion on the reactant to form the presently defined compounds.

A third aspect of the invention is an aqueous solution monopropellant consisting essentially of from about 60 to about 85 percent by weight HAN and from about 5 to about 30 percent by weight of a cubane derivative as defined in the previously stated formula, dissolved in from about 10 to about 20 percent by weight water.

A fourth aspect of the invention is a method for increasing the impetus and burn rate of propellants made up of hydroxylammonium nitrate and a fuel. This method is practiced by using the novel compounds described above as at least part of the fuel in such propellants.

DETAILED DESCRIPTION OF THE INVENTION

The present compounds have the following formula:

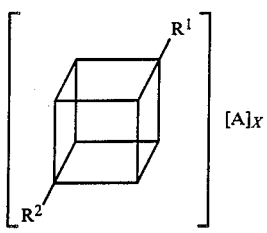

wherein $R^1$, $R^2$, A and X are all as previously defined. These are believed to be ionic compounds, and therefore the molecular formula indicates a ratio of anions and cations, rather than the makeup of a single molecule. The oxidizing anion, A, is any anion useful to provide oxidizing capability in a propellant formulation. Examples of such anions are nitrate, chlorate, perchlorate, hexafluorophosphate ($PF_6^-$) and fluoroborate ($BF_4^-$). For some applications, particularly gun propellants, it is desirable to provide a halogen free anion to avoid creation of corrosive combustion products, in which case the chlorate, perchlorate, hexafluorophosphate, and fluoroborate previously named are not suitable. Other propellants, such as rocket propellants, can have halogens in the oxidizing anion.

Preferred compounds within the scope of the preceding generic formula have the following common name and precise name: Cubane-1,4-bis(ammonium nitrate), or 1,4-bis(ammonium)pentacyclo[$4.2.0.0^{2,5}.0^{3,8}.0^{4,7}$]octane dinitrate; cubane ammonium nitrate, or pentacyclo[$4.2.0.0^{2,5}.0^{3,8}.0^{4,7}$]octylammonium nitrate; 1,4-bis-[ammonium perchlorate), or 1,4-bis-(ammonium)pentacyclo[$4.2.0.0^{2,5}.0^{3,8}.0^{4,7}$]octane diperchloroate; and cubane ammonium perchlorate, for pentacyclo[$4.2.0.0^{2,5}.0^{3,8}.0^{4,7}$]octylammonium perchlorate.

These compounds can be synthesized from corresponding compounds having different anions by an ion exchange process. The ion exchange resin should be a strongly basic anion exchange resin, one example of which is Dowel-1X8-200 chloride, made by Dow Chemical Company, Midland, Mich. This resin is an 8 percent crosslinked anionic exchange resin having particles small enough to pass through a number 100 mesh screen (U.S. Standard Sieve Series) and large enough to be retained on a 200 mesh screen. It is contemplated that any other strongly basic anionic exchange resin will also be useful in this regard. Such resins are typically tetraalkylammonium hydroxides.

In the anion exchange reaction, an oxidizing anion which is intended for the final compound is first introduced onto the reactive sites of the anion exchange resinn. This is done in the well known manner, typically involving forming a solution of a salt of the desired anion and passing the solution through a column filled with the ion exchange resin. For example, a solution of a salt selected from sodium perchlorate, sodium chlorate, sodium nitrate, or the like can be passed through an anion exchange resin column to attach its oxidizing anions to the reactive sites on the column. This process is sometimes referred to herein as charging the resin with the selected oxidizing anion.

Once the resin has been charged, an ionic cubane reactant having a different anion than the oxidizing anion with which the resin is charged is selected. Here, a convenient choice is the hydrochloride derivative (in which A is chloride and X is one). The chosen cubane reactant is dissolved in a suitable solvent, such as methanol, and the solution is passed through the column. The product then forms and is eluted with a solvent, such as a mixture of ethanol and water. The solvent can then be removed from the product, such as by applying vacuum and distilling it away, and the compound can optionally be recrystallized to further purify it.

The presence of oxidizing anions and a cubane nucleus in the novel compounds of this invention improves their utility as propellant fuels by increasing the impetus and burn rate of the propellant containing them. The advantage of the cubane nucleus is its high heat of formation. (Cubane has an extremely high steric strain.) The high density of cubane derivatives compared to other hydrocarbons also gives propellants containing them a high volumetric impetus.

In propellants made according the present invention, the preferred cubane derivatives are employed primarily as a fuel, although as noted above, they also contribute some of the function of the oxidizer. While cubane derivatives and other fuels can be combined in a propellant formulation within the scope of the present invention, cubane derivatives as described herein are optimally used as the only fuel component of a propellant formulation.

A typical liquid solution monopropellant formulation contemplated for use herein consists essentially of from about 60 to about 85 percent by weight HAN and from about 5 to about 30 percent by weight of a cubane derivative according to the present invention, dissolved in from about 10 to about 20 percent by weight water. If the cubane derivatives is cubane-1,4-bis(ammonium nitrate) (CBAN), an optimized formulation is contemplated to be:

| HAN | 67.2 wt. % |
| CBAN | 22.8 wt. % |
| Water | 10.0 wt. % |
| Total | 100.0 wt. % |

This represents a weight ratio of HAN:CBAN of 2.95:1 (the molar ratio is 8:1) and minimal water. If the cubane derivative is cubane ammonium nitrate (CAN), an optimized formulation is contemplated to be:

| HAN | 74.4 wt. % |
| CAN | 15.6 wt. % |
| Water | 10.0 wt. % |
| Total | 100.0 wt. % |

The latter formulation represents a weight ratio of HAN:CAN of 4.75:1 (the molar ratio is 9:1). Again, the amount of water is minimal.

EXAMPLE 1

Formulation of cubane-1,4-dicarboxylic acid from dimethyl ester

Cubane-1,4-dicarboxylic acid dimethyl esther purchased from Enichem Sintesi SpA (3.10 g, 14.1 mmol) was dissolved in 75 ml of hot methanol in a 250 ml, round-bottomed flask equipped with a condenser. Solid NaOH (ACS grade 0.560 g, 14.1 mmol) was added, and the reaction mixture was refluxed under $N_2$ for 13–15 h, then cooled to room temperature. The reaction mixture was diluted with 120 ml of water and extracted with ether (1×75 ml, 3×25 ml). The combined organic layer was dried over Na₂SO₄, filtered, and concentrated, leaving 373 mg (12%) of recovered starting material. The aqueous layer was acidified to pH 3 with 6N HCl and then extracted with chloroform (4×50 ml). The aqueous layer was then acidified to pH 2, saturated with sodium chloride, and extracted with ethyl acetate (3×50 ml).). The combined organic phase left 211 mg (8%) of cubane-1,4-diacid after drying over sodium sulfate, filtration, and evaporation.

EXAMPLE 2

1,4-Bis[(tert-butoxycarbonyl)amino]cubane

To a stirred solution of 16.0 g (58 millimoles) of diphenylphosphoryl azide, 6.2 g (60 millimoles) of triethylamine, and 70 ml of tert-butyl alcohol was added 5.0 g (26 millimoles) of cubane-1,4-dicarboxylic acid. The mixture was slowly brought to reflux over a 2 hour period and held at reflux for 20 hours. After being allowed to cool, the mixture was poured into 500 ml of saturated, aqueous sodium bicarbonate and stirred vigorously for 1 hour. The solid carbamate (8.7 g, 100%) was filtered, washed with water and dried. The product was used without further purification. The product decomposed at 200° C. (without melting). An infrared spectrum of the product, run in a potassium bromide pellet, had peaks at the following frequencies: 3301, 1703, 1677, 1523, 1285, and 1175 cm$^{-1}$.

EXAMPLE 3

Cubane 1,4-bis(ammonium chloride)

Hydrogen chloride gas was bubbled through a suspension of 8.0 g (22 millimoles) of 1,4-bis[tert-butoxycarbonyl]amino]cubane in 200 ml of wet methanol at −30° C. until the mixture became homogeneous. The methanol was removed in vacuo, and 20 ml of acetone was added to the residue. The precipitate (4.2 g, 85%) was filtered, washed with acetone, and dried. The light tan solid was used without further purification. The product decomposed at 220° C. (without melting). An infrared spectrum of the product, run in a potassium bromide pellet, had peaks at the following frequencies: 3100–2700, 1673, 1454, 1317, and 1078 cm$^{-1}$.

EXAMPLE 4

Synthesis of Cubane-1,4-bis(ammonium nitrate)

125 grams of the previously identified DOWEX resin were placed in a 2 inch diameter column and washed with 500 ml. of distilled water. The resin was then washed with 30% by weight aqueus sodium nitrate solution until the eluate gave a negative chloride test with silver nitrate. The resin was then washed with 1 liter of distilled water. 2.4 g (12 millimoles) of 1,4-diaminoculbane dihydrochloride dissolved in 25 ml of water was run into the column. Then the product was eluted with distilled water. The water was removed in vacuo to afford 2.7 g of a tan solid which was redissolved in 15 ml of warm distilled water and diluted with 200 ml of methanol. Cubane-1,4-bis(ammonium nitrate) was precipitated by the slow addition of 300 ml. of diethyl ether. 1.9 g (65%) of an off-white solid was obtained. Its melting point was 185° C. An infrared spectrum of the product, run in a potassium bromide pellet, had peaks at the following frequencies: 3166–2825, 1495, 1375, and 1343 cm$^{-1}$. An NMR spectrum of the product dissolved in fully deuterated dimethyl sulfoxide had peaks assigned the following sigma values, compared to tetramethylsilane: 8.6 ppm (broad singlet, 6 hydrogens), and 4.0 ppm (singlet, 6 hydrogens).

EXAMPLE 5

Synthesis of carboxycubane

Cubane-1,4-dicarboxylic acid dimethyl ester (3.10 g, 14.1 mmol) purchased from Enichem Sintesi SpA, was dissolved in 75 ml of hot methanol in a 250 ml, round-bottomed flask equipped with a condenser. Solid NaOH (ACS grade 0.560 g, 14.1 mmol) was added, and the reaction mixture was refluxed under N₂ for 13–15 h, then cooled to room temperature. The reaction mixture was diluted with 120 ml of water and extracted with ether (1×75 ml, 3×25 ml). The combined organic layer was dried over Na₂SO₄, filtered, and concentrated, leaving 373 mg (12%) of recovered starting material. The aqueous layer was acidified to pH 3 with 6N HCl and then extracted with chloroform (4×50 ml). The combined organic phase was dried over sodium sulfate, filtered, and concentrated furnishing 2.25 g (77%) of 1-carboxy-4-carbomethoxycubane as a white powder having a melting point of 178°–179° C. An NMR spectrum of the product at 500 MHz, dissolved in deuterated chloroform, had peaks assigned the following sigma values: 4.27 ppm (multiplet, 6 hydrogens) and 3.71 ppm (singlet, 3 hydrogens).

1-Carboxy-4-carbomethoxycubane (2.0 g, 9.7 mmol) was dissolved in freshly distilled oxalyl chloride (10 ml) over 0.5 hour at room temperature (gas evolution), then the solution was refluxed with stirring for 0.5 hour (using an oil bath, not a heating mantle). The mixture was cooled to room temperature; the excess oxalyl chloride was removed on the rotary evaporator (bath temperature ≦40° C.). The solid remaining was pumped at about 1 torr for 5–10 minutes. Dry benzene (20 ml) was added, followed by 1.6 g (11 mmol) of 1-hydroxypyridine-2-thione sodium salt (purchased from Sigma-Aldrich Corporation, St. Louis, Mo.; dried at 0.2 torr at room temperature for two hours) and 4-N,N-dimethylaminopyridine (71 mg, 0.58 mmol). The reaction flask was wrapped in aluminum foil to exclude light. The mixture was refluxed with stirring for 1 hour under nitrogen. 2-Methyl-2-propanethiol (2.7 ml, 23 mmol) and azobisiisobutyronitrile (96 mg, 0.58 mmol) were added; the foil was removed, and the mixture was refluxed for 2 hours. It was cooled to room temperature, diluted with 50 ml of ether, and the whole washed with 30 ml of saturated, aqueous potassium carbonate, 30 ml of 3N HCl, then 30 ml of brine. The combined aqueous extract was washed with two 50-ml of portions of ether. The organic layers were combined, dried over sodium sulfate, filtered and concentrated under vacuum. The residual brown oil was dissolved in 30 ml of toluene, and 30 ml of 15% aqueous NaOH was added. This mixture was refluxed overnight, cooled to room temperature, and separated. The organic layer was washed with two 30 ml portions of water. The combined aqueous layer was extracted with ether (2×30 ml), acidified to pH 2–3 while being kept cool, and extracted repeatedly with ethyl acetate (8×30 ml). The combined organic layer was washed with brine, dried over sodium sulfate and filtered twice through small pads of silica gel (230 mesh then 60–200 mesh), eluting with ethyl acetate. The pale yellow solution was then concentrated, affording 0.97 grams (68%) of cubane caroboxylic acid as beige crystals: crystallization from hexane give pure material having a melting point of 125°–126° C. An NMR spectrum taken at 500 MHz in deuterated chloroform showed peaks at sigma values of 10.5-11.0 ppm (broad singlet), 4.8 ppm (multiplet, 3 hydrogens), and 4.0 ppm (multiplet, 4 hydrogens).

EXAMPLE 6

(tert-Butoxycarbonyl)aminocubane

To a stirred solution of 7.6 g (28 millimoles) of diphenylphosphoryl azide, 2.9 g (29 millimoles) of triethylamine, and 40 ml of tert-butyl alcohol was added 4.0 g (27 millimoles) of carboxycubane. The mixture was slowly brought to reflux over a 2 hour period and held there for 18 hours. After being allowed to cool, the reaction mixture was poured into 200 ml of saturated, aqueous sodium bicarbonate and stirred vigorously for 1 hour. The precipitate (4.9 g, 85%) was filtered, washed with water, and dried. The carbamate was used without further purification. An NMR spectrum of the product dissolved in deuterated chloroform had peaks assigned the following sigma values, compared to tetramethylsilane: 5.2 ppm (singlet, 1 hydrogen). An infrared spectrum of the product, run in a potassium bromide pellet, had peaks at the following frequencies: 2978, 1715, 1361, and 1167 cm$^{-1}$.

EXAMPLE 7

Cubane ammonium chloride

HCl gas was bubbled through a suspension of 4.0 g (18.3 millimoles) (tert-butoxycarbonyl)aminocubane in 200 ml of wet methanol at $-30°$ C. until the solution became homogeneous. The methanol was removed in vacuo and 50 ml ether/acetone (4:1) was added to the residue. The solid (2.4 g, 85%) was collected by filtration and dried. The light tan solid was used without further purification. An NMR spectrum of the product dissolved in fully deuterated dimethyl sulfoxide had peaks assigned the following sigma values, compared to tetramethylsilane: 8.9 ppm (broad singlet, 3 hydrogens) and 4.3-3.8 (multiplet, 7 hydrogens).

EXAMPLE 8

Synthesis of Cubane Ammonium Nitrate 100 g of Dowex-1X8-200 chloride anion exchange resin were placed in a 2 inch (5.08 cm.) diameter column and washed with 500 ml of distilled water. The resin was then charged with a 30% by weight aqueous solution of sodium nitrate until the eluate gave a negative chloride test with silver nitrate. 2.3 g (14.8 mmol) of cubane ammonium chloride dissolved in 20 ml of methanol was passed through the column, then the product was eluted with a solution of 90% by weight ethanol in water. The solvent was removed in vacuo. The residue was dissolved in 50 ml of warm methanol, and cubane ammonium nitrate was precipitated by the slow addition of ether. The white solid (2.3 g, 85%) was collected by filtration and dried. Its melting point was 158° C. An infrared spectrum of the product, run in a potassium bromide pellet, had peaks at the following frequencies: 3600-3200, 1384, 1356, and 1123 cm$^{-1}$. An NMR spectrum of the product dissolved in fully deuterated dimethyl sulfoxide had peaks assigned the following sigma values, compared to tetramethylsilane: 8.6 ppm, (broad singlet, 3 hydrogens) and 4.25-3.8 ppm (multiplet, 7 hydrogens).

What is claimed is:

1. A compound having the following formula:

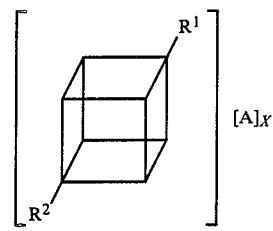

wherein R$^1$ is

R$^2$ is selected from R$^1$, in which case X is 2 divided by the valence of A, and hydrogen, in which case X is 1 divided by the valence of A; and A is an oxidizing anion useful to provide oxidizing capability in a propellant formulation.

2. 1,4-bis(ammonium)pentacyclo[4.2.0.0$^{2,5}$.0$^{3,8}$.0$^{4,7}$]octane dinitrate.

3. Pentacyclo[4.2.0.0$^{2,5}$.0$^{3,8}$.0$^{4,7}$]octyl ammonium nitrate.

4. 1,4-bis(ammonium)pentacyclo[4.2.0.0$^{2,5}$.0$^{3,8}$.0$^{4,7}$]octane diperchlorate.

5. A liquid propellant consisting essentially of:
   A. from about 60% to about 85% by weight of hydroxylammonium nitrate;
   B. from about 30% by weight of a compound according to claim 1; and
   C. from about 10% to about 20% water.

6. A liquid propellant consisting essentially of:
   A. from about 60% to about 85% by weight of hydroxylammonium nitrate;
   B. from about 5% to about 30% by weight of a compound having the following formula:

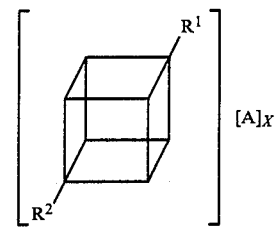

wherein R$^1$ and R$^2$ are

A is nitrate, and X is 2; and
   C. from about 10% to about 20% water.

7. A compound having the following formula:

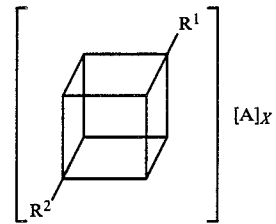

wherein $R^1$ is

$R^2$ is selected from $R^1$, in which case X is 2 divided by the valence of A, and hydrogen, in which case X is 1 divided by the valence of A; and A is an anion selected from nitrate, chlorate, perchlorate, hexafluorophosphate, and fluoroborate.

8. A liquid propellant consisting essentially of:
   A. from about 60% to about 85% by weight of hydroxylammonium nitrate;
   B. from about 5% to about 30% by weight of a compound according to claim 7; and
   C. from about 10% to about 20% water.